United States Patent [19]

Nelson et al.

[11] Patent Number: 5,204,265

[45] Date of Patent: Apr. 20, 1993

[54] METHOD OF STABILIZING A CARBON DIOXIDE SENSOR

[75] Inventors: Alan Nelson, San Diego; Henry K. Hui, Laguna Niguel; Monte Bennett, Escondido; Soonkap Hahn, Poway; Charles S. Bankert, Oceanside, all of Calif.

[73] Assignee: Puritan-Bennett Corporation, Carlsbad, Calif.

[21] Appl. No.: 933,884

[22] Filed: Aug. 21, 1992

Related U.S. Application Data

[63] Continuation of Ser. No. 597,816, Oct. 15, 1990, abandoned.

[51] Int. Cl.$^5$ .............. G01N 31/00; G01C 17/38; A61B 5/05
[52] U.S. Cl. .............................. 436/8; 436/11; 436/164; 436/172; 73/1 R; 73/23.21; 204/463; 204/415; 128/635
[58] Field of Search .............. 128/635; 204/403, 415; 436/8, 11, 164, 172; 73/23.21, 1 R

[56] References Cited

U.S. PATENT DOCUMENTS

| | | | |
|---|---|---|---|
| 3,754,867 | 8/1973 | Guenther et al. | 23/254 R |
| 3,824,157 | 7/1974 | Macur | 436/68 X |
| 3,884,640 | 5/1975 | Lock et al. | 436/68 X |
| 4,469,562 | 9/1984 | Chang | 204/1 T |
| 4,474,183 | 10/1984 | Yano et al. | 128/635 |
| 4,689,308 | 8/1987 | Gerhard | 436/19 X |
| 4,834,101 | 5/1989 | Collison et al. | 128/635 |
| 4,840,179 | 6/1989 | Ullrich | 128/633 |

FOREIGN PATENT DOCUMENTS

0105870A2  4/1984  European Pat. Off. .

OTHER PUBLICATIONS

Wolfbeis, et al., "Fiber-Optic Fluorosensor for Oxygen and Carbon Dioxide" (Anal. Chem. 1988).
Munkholm, et al., "A Fiber-Optic Sensor for $CO_2$ Measurement" (vol. 35, 1988).
Published application PB83-189738 (Vurek) "Fiber-Optic Carbon Dioxide Partial Pressure Sensor" Mar. 1, 1983.

Primary Examiner—James C. Housel
Assistant Examiner—N. Bhat
Attorney, Agent, or Firm—Fulwider Patton Lee & Utecht

[57] ABSTRACT

The method of stabilizing a carbon dioxide sensor involves treatment of the sensor to reduce the instability that may occur in carbon dioxide sensors when such sensors are exposed to either very low or very high carbon dioxide levels for extended periods of time. This is accomplished by storing the sensor in an aqueous solution containing at least 2 weight percent carbon dioxide, for from several days to several months. The solution may be prepared in advance, or may be dynamically infused with carbon dioxide to provide the desired carbon dioxide content.

6 Claims, No Drawings

METHOD OF STABILIZING A CARBON DIOXIDE SENSOR

This application is a continuation of application Ser. No. 07/597,816, filed Oct. 15, 1990, now abandoned.

BACKGROUND OF THE INVENTION

1. Field of the Invention

This invention is generally directed to chemical and biochemical analysis of an analyte in a fluid or gaseous mixture, and more specifically relates to methods of stabilizing measurements taken with an intravascular carbon dioxide sensor.

2. Description of Related Art

Measurement of acidity (pH) and the tension or partial pressure of carbon dioxide and oxygen in the blood have become important in modern medicine, particularly with regard to determining the respiratory condition of a patient. Although electrodes have been developed which are capable of making such measurements, they are generally of limited use in the medical field. Optical sensors for taking intravascular measurements of acidity, carbon dioxide and oxygen levels in the blood have also been developed, based upon the principle of enclosing a fluorescent indicator within a membrane permeable to the analyte to be measured, coupled to one or more optical fibers for measuring the intensity of fluorescence from the indicator. Since the fluorescence reaction of appropriately chosen indicators is altered according to the level of acidity, carbon dioxide, or oxygen being measured, these sensors allow remote measurement of these parameters when combined with compatible intravascular catheter systems.

A fiber optic chemical sensor may also be used for measuring pH by the use of optical absorbance indicators, such as phenol red, which may be chemically bound in the sensor. In this type of pH sensor, green and red light typically emerge from one optical fiber into the sensor, passing through the dye, to be reflected back through an optical fiber to a detector system. The green light is absorbed by the base form of the indicator, and the red light is not absorbed by the indicator, so that the red light may be used as an optical reference. The ratio of green to red light can then be measured, and related to pH.

A fluorescent indicator may be used in a similar fashion, with light in one wavelength region being used to excite the fluorescent indicator dye to emit light of a different wavelength. Such optical pH sensors typically include a fluorescent indicator dye, such as fluorescein or hydroxypyrenetrisulfonic acid (HPTS), placed over the tip of an optical fiber and a membrane cover over the dye which is permeable to the hydronium ions to be measured. The dye fluoresces when exposed to a certain wavelength of light conducted to it by the optical fiber. In practice, a pH sensor is fabricated by immobilizing a pH sensitive dye into a matrix attached to the distal end of the fiber. The dye . is typically capable of existing in two forms, an anionic or base form, and a protonated or acid form. The two forms are each excited by a different frequency, but fluoresce at the same frequency, with the output responsive to excitation at the appropriate different frequencies being proportional to the pH of the sample to which the sensor is exposed. In this manner, measurement of the intensity of fluorescence of the indicator dye can be related to pH. A clinically useful range for measuring carbon dioxide as a blood gas parameter has been found to be from about 1.4 weight percent to about 15 weight percent carbon dioxide. Therefore, it is desirable for a carbon dioxide sensor to be accurate and repeatable over at least this range.

It has also been found that carbon dioxide sensors frequently become destabilized when exposed to low carbon dioxide levels, and that a progressive loss of fluorescent intensity occurs in sensors utilizing fluorescent indicators after exposure to high carbon dioxide concentrations. The instability of such fiber optic based carbon dioxide sensors when the sensors are exposed to either very low or very high carbon dioxide levels for prolonged periods of time, such as several days, frequently results in non-specific drift of measurements of carbon dioxide levels. It would therefore be desirable to provide a carbon dioxide blood gas sensor which mitigates this non-specific drift instability.

SUMMARY OF THE INVENTION

Briefly, and in general terms, the present invention provides a new and improved method of stabilizing a carbon dioxide sensor which is adapted for measuring concentrations of carbon dioxide in a fluid. The invention functions by exposing the sensor to a preparatory solution which is infused with elevated levels of carbon dioxide.

Basically, the present invention is directed to an improved method of reducing the instability that may occur in carbon dioxide sensors when such sensors are exposed to either very low or very high carbon dioxide levels for extended periods of time. This is accomplished by exposing the sensor to high carbon dioxide levels for a period of time sufficient to allow the sensor to achieve measurement stability. Thus, the method of the present invention acts to decrease the initial time required to achieve drift stability compared to the use of a sensor which has not used the invention. The sensor is preferably retained in storage containers containing a solution which has been infused with a gas stream containing from 2 to 100 weight percent carbon dioxide for a period of time varying from several days to several weeks. One currently preferred method is to retain the sensor in a storage container in a prepared solution infused with approximately 8 weight percent carbon dioxide, thus statically maintaining the sensor at a carbon dioxide tension in the midrange of the physiologically significant range. It has been found that storage of the sensor in a solution which has been infused with from 2 to 100 weight percent carbon dioxide eliminates sources of non-specific long term drift that lead to inaccuracy in transduced carbon dioxide content measurements in applications in which the sensor is required to monitor arterial carbon dioxide for prolonged periods of time. This conditioning procedure also facilities faster calibration at the point of use by maintaining the sensor at a physiologically significant carbon dioxide tension immediately prior to use.

These and other objects and advantages of the invention will become apparent from the following detailed description, which illustrates, by way of example, the features of the invention.

DETAILED DESCRIPTION OF THE PREFERRED EMBODIMENTS

Problems of non-specific drift of carbon dioxide blood gas sensors have been observed in both in vitro and in vivo testing for sensor instability. According to a presently preferred embodiment of the method of the present invention, a carbon dioxide sensor is brought into a state of readiness by passive storage in a solution with a carbon dioxide tension in a physiologically significant range. In an alternative preferred embodiment, the sensor may be conditioned by a combination of exposure of the sensor to high carbon dioxide levels in a solution dynamically infused with a gas stream having very high to absolute carbon dioxide tension, followed by passive storage in another solution with a carbon dioxide tension in a physiologically significant range.

The present invention is particularly applicable for stabilizing measurements of the concentration of carbon dioxide in a fluid, such as blood, by a carbon dioxide sensor sensitive to changes in pH of a bicarbonate buffer immobilized in the sensor. A typical sensor incorporates a dye material such as fluorescein in a polymeric matrix, such as silicone, which is permeable to carbon dioxide in the blood. The sensor is typically placed at the end of an optical fiber, which may be inserted into the vasculature of a patient for in vivo blood gas measurements. The sensor is of the type sensitive to changes in pH, and the matrix material is generally soaked in a sodium bicarbonate solution, which serves as a buffer according to the well known equation:

$$CO_2(aq) + H_2O \rightleftharpoons H_2CO_3 \rightleftharpoons H^+ + HCO_3^-$$ 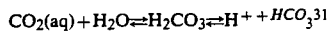

According to a first preferred embodiment of the invention, the sensor is typically stored in a sealed container having an aqueous solution which preferably has a relatively high partial pressure of carbon dioxide. The aqueous solution also is preferably osmotically adjusted to approximately match the osmotic pressure of the fluid in which the sensor will eventually be used. The solution is preferably prepared in advance, although it is also possible to infuse the solution with the proper carbon dioxide content after the sensor is placed in the solution.

The aqueous solution preferably should have at least a 2 weight percent carbon dioxide content, and can be prepared by infusing the solution with a gas stream containing from 2 to 100 weight percent carbon dioxide, with the balance being inert gas, such as nitrogen, to infuse the second solution with a physiologically significant carbon dioxide tension. The aqueous solution in which the sensor is to be stored is preferably infused with a gas containing approximately 8 weight percent carbon dioxide, with the balance of the gas being inert gas. The storage solution is also preferably osmotically adjusted to be approximately equivalent to the osmotic strength of the fluid in which the carbon dioxide sensor will eventually be used. The sensor is typically stored in a sealed container with the storage solution for at least one day, and preferably from several days to several months, to condition the sensor for calibration and use.

In another preferred embodiment, the sensor may optionally be preliminarily exposed to a preparatory aqueous solution prior to storage in a second aqueous solution. In this two step process, the sensor is exposed to a preparatory aqueous solution, while a gas stream having a relatively high partial pressure of carbon dioxide, and preferably approximately 100 weight percent carbon dioxide, is periodically or continuously dynamically infused into the solution by bubbling the gas stream in the solution for an hour to a few days as desired.

The sensor is then stored in the second aqueous solution having a 2 weight percent carbon dioxide content of approximately 2 weight percent or more. The second solution in which the sensor is to be stored is preferably prepared in advance, but may optionally be dynamically prepared after the sensor has been placed in the solution by infusing a gas stream containing from 2 to 100 weight percent carbon dioxide, with the balance being inert gas, such as nitrogen, to infuse the second solution with a physiologically significant carbon dioxide tension. The physiologically significant range of carbon dioxide concentration for the gas stream is typically from 2 weight percent to 15 weight percent carbon dioxide, with the balance of the gas being inert gas, and the secondary aqueous solution is preferably infused with a gas containing approximately 8 weight percent carbon dioxide, with the balance of the gas being inert gas. The secondary solution is also preferably osmotically adjusted to be approximately equivalent to the osmotic strength of the fluid in which the carbon dioxide sensor will eventually be used. The sensor is then typically stored in a sealed container with the second solution to which the sensor is exposed for at least one day, and preferably from several days to several months, to condition the sensor for calibration and use.

It has been found that carbon dioxide sensors such as those discussed above provide substantially stabilized measurements of carbon dioxide tension for in vitro and in vivo blood gas measurements, not exhibiting the previously observed non-specific drift in measurements of either low or high carbon dioxide levels in solutions for prolonged periods of time. The method also enables faster calibration at the point of use by maintaining the sensor at a physiologically significant carbon dioxide tension.

It should be recognized that other forms of carbon dioxide sensors, such as pH electrodes measuring changes in pH of bicarbonate buffers, or similar buffers, may also be stabilized by the method of the invention.

It will be apparent from the foregoing that, while particular forms of the invention have been described, various modifications can be made without departing from the spirit and scope of the invention. Accordingly, it is not intended that the invention be limited, except as by the appended claims.

What is claimed is:

1. A method of stabilizing non-specific drift of an optical fiber carbon dioxide sensor adapted for measurement of the concentration of carbon dioxide in a fluid, comprising the steps of:

exposing the sensor to a first aqueous solution infused with a concentration of carbon dioxide which is higher than a normal physiologically significant blood level of carbon dioxide for at least one hour; and exposing the sensor for at least one day to a second aqueous solution infused with a gas consisting essentially of from 2 weight percent to 15 weight percent of carbon dioxide, with the balance of the gas being inert.

2. The method of claim 1, wherein the sensor is exposed to the first aqueous solution while the first aqueous solution is dynamically infused by bubbling the first aqueous solution with a gas stream consisting essentially of 100 weight percent of carbon dioxide.

3. The method of claim 1, wherein the second aqueous solution is infused with a gas consisting essentially of approximately 8 weight percent carbon dioxide, with the balance of the gas being inert.

4. The method of claim 1, wherein the second aqueous solution is infused with a gas consisting essentially of approximately 8 weight percent carbon dioxide, with the balance of the gas being inert gas.

5. A method of stabilizing non-specific drift of an optical fiber carbon dioxide sensor adapted for measurement of a concentration of carbon dioxide in a fluid, comprising the steps of:

exposing the sensor to a first aqueous solution infused with a gas stream consisting essentially of 100% carbon dioxide for at least one hour; and exposing the sensor for at least one day to a second aqueous solution infused with a gas consisting of essentially of from 2 weight percent to 15 weight percent carbon dioxide, with the balance of the gas being inert.

6. The method of claim 5, wherein the second aqueous solution is infused with a gas consisting essentially of approximately 8 weight percent carbon dioxide, with the balance of the gas being inert.

* * * * *

UNITED STATES PATENT AND TRADEMARK OFFICE
CERTIFICATE OF CORRECTION

PATENT NO. : 5,204,265

DATED : April 20, 1993

INVENTOR(S) : Alan Nelson; Henry K. Hui; Monte Bennett; Soonkap Hahn; Charles S. Bankert It is certified that error appears in the above-identified patent and that said Letters Patent is hereby corrected as shown below:

Column 1, line 59, delete period appearing between "dye" and "is".

Column 3, line 25, in the equation, change "$HCO_3 31$" to read "$HCO_3^-$".

Column 4, line 5, add a space between "100" and "weight".

In the Claims:

Column 5, lines 1-13, delete double spacing.

Signed and Sealed this

First Day of February, 1994

Attest:

BRUCE LEHMAN

*Attesting Officer*  *Commissioner of Patents and Trademarks*